United States Patent [19]

Nanya et al.

[11] Patent Number: 4,990,425
[45] Date of Patent: Feb. 5, 1991

[54] TONER FOR DEVELOPING LATENT ELECTROSTATIC IMAGES

[75] Inventors: Toshiki Nanya, Mishima; Kimitoshi Yamaguchi, Numazu, both of Japan

[73] Assignee: Ricoh Company, Ltd., Tokyo, Japan

[21] Appl. No.: 334,202

[22] Filed: Apr. 5, 1989

[30] Foreign Application Priority Data

Apr. 11, 1988 [JP] Japan .................. 63-88586
Oct. 28, 1988 [JP] Japan .................. 63-272015

[51] Int. Cl.$^5$ .................. G03G 13/22; G03G 9/08
[52] U.S. Cl. .................. 430/110; 430/126
[58] Field of Search .................. 430/109, 110, 126

[56] References Cited

U.S. PATENT DOCUMENTS 4,673,631 6/1987 Fukumoto et al. .................. 430/110
4,789,615 12/1988 Ciccarelli et al. .................. 430/110

*Primary Examiner*—John Goodrow
*Attorney, Agent, or Firm*—Cooper & Dunham

[57] ABSTRACT

A dry-type toner is disclosed, which comprises as the main components a resin, a coloring agent and a negative charge controlling agent selected from the group consisting of (1) metallic salts of indolecarboxylic acid having the general formula (I);

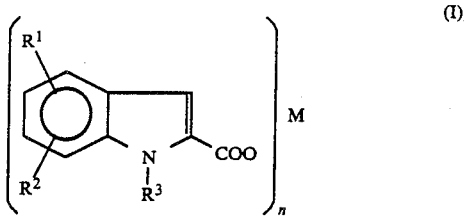

(2) metallic salts of quinolinecarboxylic acid having the general formula (II);

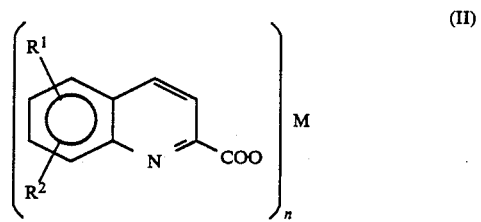

and (3) metallic salts of benzothiazole derivatives having the general formula (III):

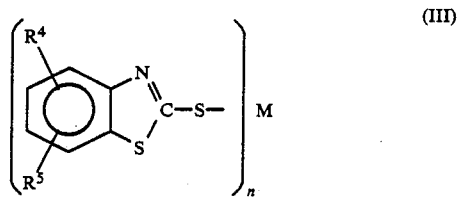

12 Claims, 1 Drawing Sheet

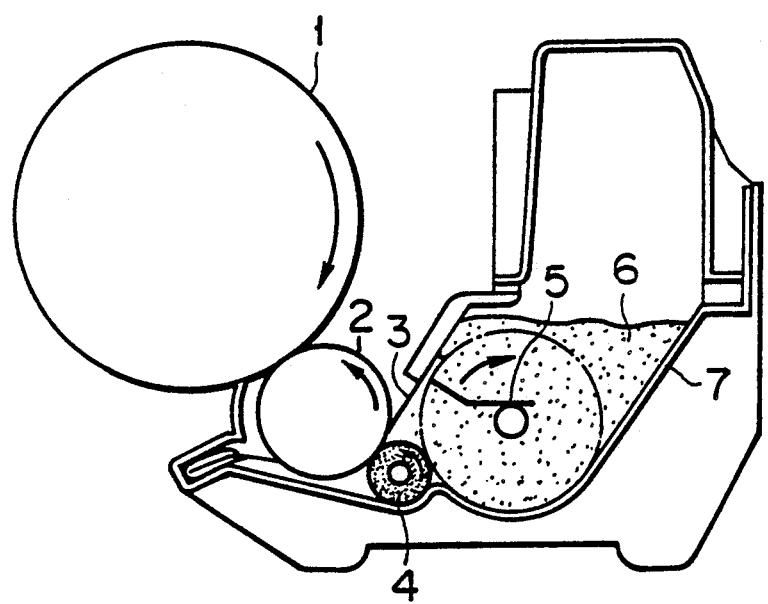

TONER FOR DEVELOPING LATENT ELECTROSTATIC IMAGES

BACKGROUND OF THE INVENTION

1. Field of the Invention

The present invention relates to a dry-type toner for developing latent electrostatic images in the field of electrophotography, electrostatic recording and electrostatic printing, and particularly to a dry-type toner for developing latent electrostatic images, comprising as a negative charge controlling agent a metallic salt compound.

2. Discussion of Background

For developing latent electrostatic images formed on an electrophotographic photoconductor or electrostatic recording member to visible toner images, there are conventionally proposed two methods: a wet-type developing method using a liquid type developer, and a dry-type developing method using a dry-type developer. This dry-type developer includes one-component dry-type developer comprising a toner obtained by dispersing a coloring agent such as a dye and a pigment in a binder resin; and a two-component dry-type developer obtained by mixing the above-mentioned toner and carrier particles. These methods have individually their own advantages and shortcomings. Recently, the dry-type developing method is more prevalant than the wet-type developing method.

When the above-mentioned dry-type developer is prepared by merely dispersing a coloring agent in a binder resin, the desired chargeability cannot be obtained. Therefore, a proper amount of a charge controlling agent is generally added to the dry-type developer.

Examples of the conventional charge controlling agent are as follows:

(1) Charge controlling agents which apply a positive charge to the toner;
Oil-soluble nigrosine dye, quaternary ammonium salt, azine-type dye having an alkyl group, basic dye, and basic dye lake.

(2) Charge controlling agents which apply a negative charge to the toner;
Metal-containing dye, for example, chromium-containing monoazo complex, chromium-containing salicylic acid compound complex, and chromium-containing organic dye such as copper phthalocyanine green and chromium-containing monoazo dye.

These conventional charge controlling agents exhibit satisfactory charge controlling performance at the initial stage when the toners comprising such charge controlling agents are used in the electrophotographic process. However, the charge controlling performance of the conventional charge controlling agents is deteriorated and triboelectric chargeability of the toner is decreased in the course of repeated use thereof, with the result that the quality of obtained toner images gradually becomes poor.

In addition, such conventional charge controlling agents are separated from the toner particles due to the friction between toner particles and between the toner particle and the surface of a photoconductor, and the collision of the toner particles with carrier particles. The charge controlling agents which have been separated from the toner are deposited on the surface of the photoconductor, and as a result, the so-called toner-filming phenomenon takes place. Particularly, the toner-filming phenomenon is apt to occur at high temperatures and high humidities.

As previously mentioned, most of the conventional charge controlling agents are coloring materials, so that each charge controlling agent can only be used for a toner whose color is the same as that of the charge controlling agent. When a color toner is prepared by containing the conventional charge controlling agents therein, clear color images cannot be readily obtained.

SUMMARY OF THE INVENTION

It is therefore an object of the present invention to provide a dry-type toner for developing latent electrostatic images, with an extended life and excellent environmental stability, capable of easily yielding clear color images without staining the photoconductor owing to the toner-filming phenomenon and without decreasing the image quality in the course of repeated operation.

The above object of the present invention can be achieved by a dry-type toner comprising as the main components a resin, a coloring agent and a colorless or light-colored negative charge controlling agent capable of imparting stable triboelectricity to the toner, which charge controlling agent is selected from the group consisting of:

(1) Metallic salts of indolecarboxylic acid having the general formula (I);

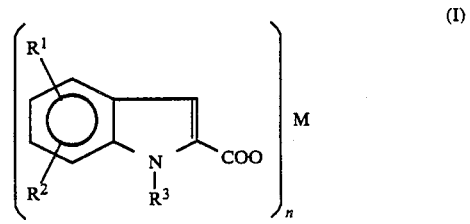

wherein $R^1$ and $R^2$, which may be the same or different, each represent hydrogen, a halogen, a nitro group, a carboxy ester group, a hydroxyl group, a sulfonamide group, a cyano group, an alkyl group having 1 to 8 carbon atoms, or an alkoxyl group having 1 to 8 carbon atoms; $R^3$ represents hydrogen or an alkyl group having 1 to 8 carbon atoms; M represents a metal element selected from the group consisting of Zn, Co, Ni, Fe, Cr, Al and Te; and n is a number equivalent to the valence number of the metal represented by M.

(2) Metallic salts of quinolinecarboxylic acid having the general formula (II);

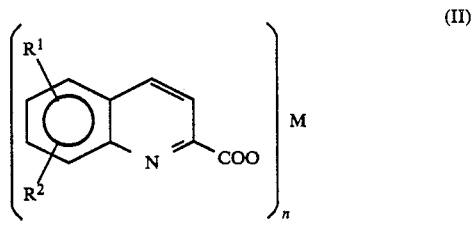

wherein $R^1$, $R^2$, M and n are respectively the same as previously defined.

(3) Metallic salts of benzothiazole derivatives having the general formula (III);

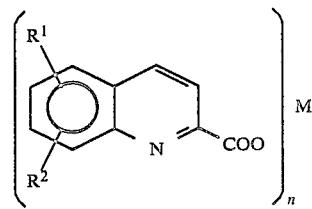

wherein $R^1$, $R^2$, M and n are the same as defined in the formula (I).

(3) Metallic salts of benzothiazole derivatives

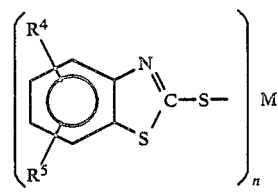

wherein $R^4$ and $R^5$, which may be the same or different, each represent hydrogen, an alkyl group having 1 to 10 carbon atoms, an amino group having 1 to 10 carbon atoms or an alkylamino group having 1 to 10 carbon atoms; M represents a metal element selected from the group consisting of Zn, Co, Ni, Fe and Te; and n is a number equivalent to the valence number of the metal represented by M.

BRIEF DESCRIPTION OF THE DRAWINGS

In the drawing, the single figure is a schematic cross-sectional view of a development unit for use in the present invention.

DETAILED DESCRIPTION OF THE PREFERRED EMBODIMENTS

The dry-type toner for developing latent electrostatic images according to the present invention comprises as the main components a resin, a coloring agent and a negative charge controlling agent.

The negative charge controlling agent for use in the present invention is selected from the group consisting of (1) metallic salts of indolecarboxylic acid represented by the formula (I); (2) metallic salts of quinolinecarboxylic acid represented by the formula (II); and (3) metallic salts of benzothiazole derivatives.

(1) Metallic salts of indolecarboxylic acid

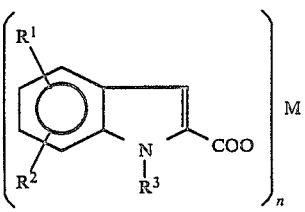

wherein $R^1$ and $R^2$, which may be the same or different, each represent hydrogen, a halogen, a nitro group, a carboxy ester group, a hydroxyl group, a sulfonamide group, a cyano group, an alkyl group having 1 to 8 carbon atoms, or an alkoxyl group having 1 to 8 carbon atoms; $R^3$ represents hydrogen or an alkyl group having 1 to 8 carbon atoms; M represents a metal element selected from the group consisting of Zn, Co, Ni, Fe, Cr, Al and Te; and n is a number equivalent to the valence number of the metal represented by M.

(2) Metallic salts of quinolinecarboxylic acid

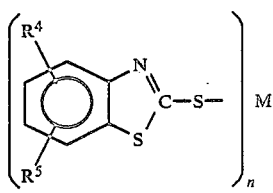

wherein $R^4$ and $R^5$, which may be the same or different, each represent hydrogen, an alkyl group having 1 to 10 carbon atoms, an amino group having 1 to 10 carbon atoms or an alkylamino group having 1 to 10 carbon atoms; M represents a metal element selected from the group consisting of Zn, Co, Ni, Fe and Te; and n is a number equivalent to the valence number of the metal represented by M.

The above-mentioned three types of the metallic salts can be prepared by the conventional methods.

In the case of the metallic salt of indolecarboxylic acid, for example, an aqueous solution of an indolecarboxylic acid is neutralized by alkali. To this solution, an aqueous solution of the corresponding metallic salt is added to exchange the metals.

The metallic salt of quinolinecarboxylic acid can be obtained in the same manner as the above. The metallic salt of benzothiazole derivatives can be obtained by adding an aqueous solution of the corresponding metallic salt to an aqueous solution of the corresponding benzothiazole derivative to exchange the metals.

The present invention will now be explained in detail by referring to the following synthesis examples of the previously mentioned metallic salts.

SYNTHESIS EXAMPLE 1

0.1 mole of indolecarboxyl acid was dissolved in 50 ml of water, under application of heat to 70° C. To this solution, 0.1 mole of sodium hydroxide was added for the neutralization of the solution. After the completion of neutralization of the solution, 0.05 moles of $ZnSO_4 \cdot 7H_2O$ was added thereto. At first there appeared a milky turbidity in the solution, and then zinc salt of indolecarboxylic acid of the following formula was obtained in the form of a white precipitate.

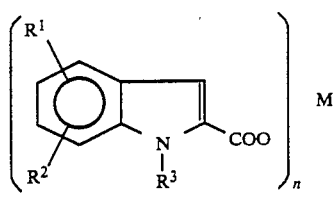

wherein $R^1$, $R^2$, and $R^3$ each represent hydrogen; and M represents zinc.

SYNTHESIS EXAMPLE 2

Synthesis Example 1 was repeated except that the indolecarboxylic acid employed in Synthesis Example 1 was replaced by quinolinecarboxylic acid, whereby zinc salt of quinolinecarboxylic acid of the following formula was obtained in the form of a white precipitate.

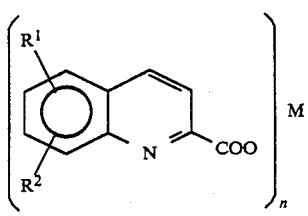 (II)

wherein $R^1$ and $R^2$ each represent hydrogen; and M represents zinc.

SYNTHESIS EXAMPLE 3

An aqueous solution of zinc sulfate was added to an aqueous solution of sodium salt of 2-mercaptobenzothiazole, whereby zinc salt of 2-mercaptobenzothiazole of the following formula was obtained.

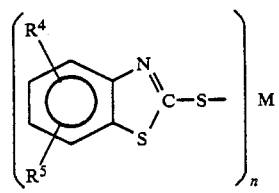 (III)

wherein $R^4$ and $R^5$ each represent hydrogen; and M represents zinc.

Specific examples of the above-mentioned metallic salts represented by the formulas (I), (II) and (III) are as follows:

| Metallic Salt No. | Chemical Formula |
|---|---|
| I-(1) | [indole-COO]$_2$Zn (N-H) |
| I-(2) | [indole-COO]$_2$Zn (N-CH$_3$) |
| I-(3) | [indole-COO]$_2$Cr (N-H) |
| I-(4) | [indole-COO]$_2$Zn (N-nC$_4$H$_9$) |
| I-(5) | [4,6-di-tC$_4$H$_9$-indole-COO]$_2$Zn (N-C$_2$H$_5$) |
| I-(6) | [5-nC$_8$H$_{17}$-indole-COO]$_2$Cr (N-H) |
| I-(7) | [4,6-di-CH$_3$-indole-COO]$_2$Zn (N-H) |
| I-(8) | [4-tC$_4$H$_9$-6-C$_2$H$_5$-indole-COO]$_2$Co (N-C$_3$H$_7$) |
| I-(9) | [5-CH$_3$O-indole-COO]$_2$Ni (N-CH$_3$) |

| Metallic Salt No. | Chemical Formula |
|---|---|
| I-(10) | 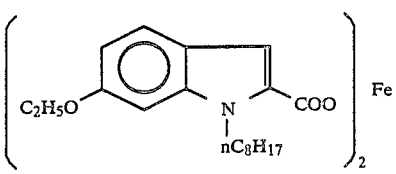 |
| I-(11) | 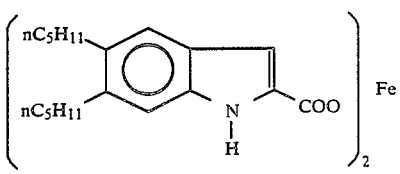 |
| I-(12) | 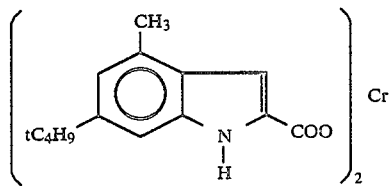 |
| I-(13) | 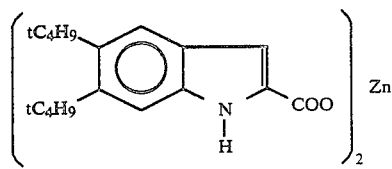 |
| I-(14) | 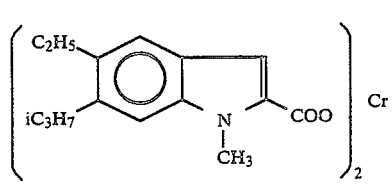 |
| I-(15) | 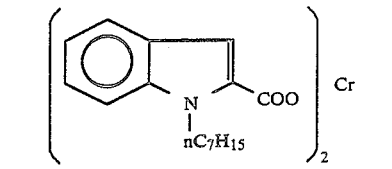 |
| I-(16) | 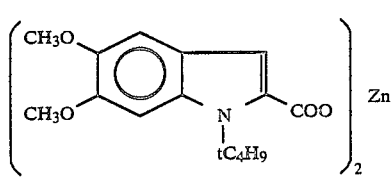 |
| I-(17) | 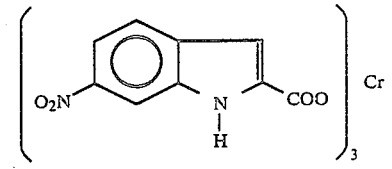 |
| I-(18) | 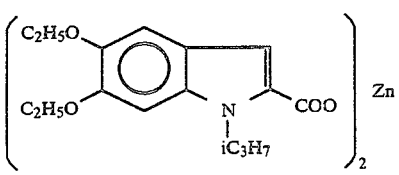 |
| I-(19) | 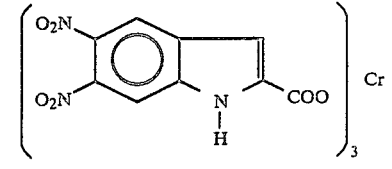 |
| I-(20) | 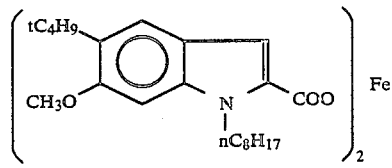 |
| I-(21) | 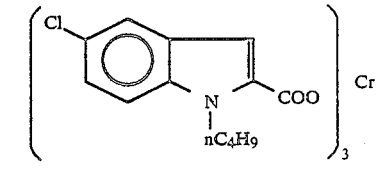 |
| I-(22) | 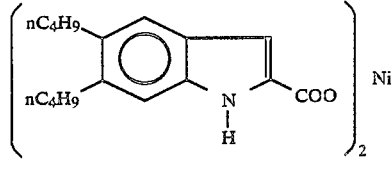 |
| I-(23) | 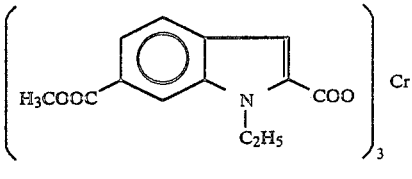 |
| I-(24) | 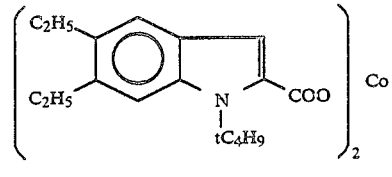 |
| I-(25) | 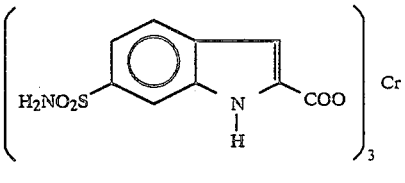 |

-continued

| Metallic Salt No. | Chemical Formula |
|---|---|
| I-(26) | {[3,4-dihydroxy-N-(iC3H9)-indole-2-carboxylate]}3 Cr |
| I-(27) | {[5-cyano-indole-2-carboxylate, NH]}3 Cr |
| I-(28) | {[5-chloro-6-cyano-N-(nC4H9)-indole-2-carboxylate]}3 Cr |
| I-(29) | {[5,6-dinitro-indole-2-carboxylate, NH]}2 Zn |
| I-(30) | {[5,6-dichloro-N-(C2H5)-indole-2-carboxylate]}2 Zn |
| I-(31) | {[6-(H3COOC)-indole-2-carboxylate, NH]}2 Zn |
| I-(32) | {[6-HO-N-(nC4H9)-indole-2-carboxylate]}3 Al |
| I-(33) | {[6-NC-indole-2-carboxylate, NH]}3 Al |

-continued

| Metallic Salt No. | Chemical Formula |
|---|---|
| I-(34) | {[5,6-dinitro-N-(CH3)-indole-2-carboxylate]}2 Fe |
| I-(35) | {[5-Br-6-Cl-N-(CH3)-indole-2-carboxylate]}2 Fe |
| I-(36) | {[6-(H5C2OOC)-N-(C2H5)-indole-2-carboxylate]}2 Ni |
| I-(37) | {[6-NC-indole-2-carboxylate, NH]}2 Ni |
| I-(38) | {[6-HO-N-(C2H5)-indole-2-carboxylate]}2 Co |
| I-(39) | {[5-O2N-indole-2-carboxylate, NH]}3 Cr |
| I-(40) | {[5,6-dinitro-indole-2-carboxylate, NH]}3 Cr |
| I-(41) | {[5-Cl-N-(nC4H9)-indole-2-carboxylate]}3 Cr |

| Metallic Salt No. | Chemical Formula |
|---|---|
| I-(42) | [H₃COOC–(indole with N–C₂H₅)–COO]₃ Cr |
| I-(43) | [H₂NO₂S–(indole with NH)–COO]₃ Cr |
| I-(44) | [HO,HO–(indole with N–iC₃H₇)–COO]₃ Cr |
| I-(45) | [NC–(indole with NH)–COO]₃ Cr |
| I-(46) | [Cl, NC–(indole with N–nC₄H₉)–COO]₃ Cr |
| I-(47) | [O₂N, O₂N–(indole with NH)–COO]₂ Zn |
| I-(48) | [Cl, Cl–(indole with N–C₂H₅)–COO]₂ Zn |
| I-(49) | [H₃COOC–(indole with NH)–COO]₂ Zn |
| I-(50) | [HO–(indole with N–nC₄H₉)–COO]₃ Al |
| I-(51) | [NC–(indole with NH)–COO]₃ Al |
| I-(52) | [O₂N, O₂N–(indole with NH)–COO]₂ Fe |
| I-(53) | [Br, Cl–(indole with NH)–COO]₂ Fe |
| I-(54) | [H₃C₂OOC–(indole with N–C₂H₅)–COO]₂ Ni |
| I-(55) | [NC–(indole with NH)–COO]₂ Ni |
| I-(56) | [HO–(indole with N–C₂H₅)–COO]₂ Co |
| II-(1) | [quinoline-2-COO]₂ Zn |
| II-(2) | [quinoline-2-COO]₂ Cr |

| Metallic Salt No. | Chemical Formula |
|---|---|
| II-(3) | (6-methylquinoline-2-carboxylate)₂ Zn |
| II-(4) | (5,6-dimethylquinoline-2-carboxylate)₂ Zn |
| II-(5) | (6-tC₄H₉-quinoline-2-carboxylate)₂ Zn |
| II-(6) | (5,7-di-tC₄H₉-quinoline-2-carboxylate)₂ Zn |
| II-(7) | (5,6-dimethoxyquinoline-2-carboxylate)₂ Zn |
| II-(8) | (5-methyl-7-ethoxyquinoline-2-carboxylate)₂ Zn |
| II-(9) | (5,6-di-nC₉H₁₇-quinoline-2-carboxylate)₂ Zn |
| II-(10) | (6-ethylquinoline-2-carboxylate)₂ Cr |
| II-(11) | (5-methoxy-7-tC₄H₉-quinoline-2-carboxylate)₂ Cr |
| II-(12) | (5,7-dimethylquinoline-2-carboxylate)₂ Cr |
| II-(13) | (7-tC₄H₉-quinoline-2-carboxylate)₂ Co |
| II-(14) | (5,6-di-iC₃H₇-quinoline-2-carboxylate)₂ Co |
| II-(15) | (5-methoxy-7-nC₇H₁₅-quinoline-2-carboxylate)₂ Ni |
| II-(16) | (5,7-di-nC₈H₁₇-quinoline-2-carboxylate)₂ Ni |
| II-(17) | (5,6-diethylquinoline-2-carboxylate)₂ Fe |
| II-(18) | (5-methoxy-6-methylquinoline-2-carboxylate)₂ Fe |
| III-(1) | (benzothiazole-2-thiolate)₂ Zn |
| III-(2) | (benzothiazole-2-thiolate)₂ Ni |
| III-(3) | (benzothiazole-2-thiolate)₂ Co |

| Metallic Salt No. | Chemical Formula |
|---|---|
| III-(4) | (benzothiazole-2-thiolate)$_2$ Fe |
| III-(5) | (benzothiazole-2-thiolate)$_4$ Te |
| III-(6) | (4-NH$_2$-benzothiazole-2-thiolate)$_2$ Zn |
| III-(7) | (5,6-di-CH$_3$-benzothiazole-2-thiolate)$_2$ Zn |
| III-(8) | (5,6-di-C$_2$H$_5$-benzothiazole-2-thiolate)$_2$ Ni |
| III-(9) | (4-CH$_3$-benzothiazole-2-thiolate)$_2$ Fe |
| III-(10) | (4,7-di-nC$_4$H$_9$-benzothiazole-2-thiolate)$_2$ Co |
| III-(11) | (4-NH$_2$-benzothiazole-2-thiolate)$_2$ Co |
| III-(12) | (4-CH$_3$-6-CH$_3$-benzothiazole-2-thiolate)$_2$ Zn |
| III-(13) | (7-CH$_3$-benzothiazole-2-thiolate)$_4$ Te |
| III-(14) | (7-tC$_4$H$_9$-benzothiazole-2-thiolate)$_2$ Fe |
| III-(15) | (4,7-di-tC$_4$H$_9$-benzothiazole-2-thiolate)$_2$ Ni |
| III-(16) | (7-C$_8$H$_{17}$-benzothiazole-2-thiolate)$_2$ Co |
| III-(17) | (7-N(C$_2$H$_5$)$_2$-benzothiazole-2-thiolate)$_2$ Zn |
| III-(18) | (4,7-di-N(C$_2$H$_5$)$_2$-benzothiazole-2-thiolate)$_4$ Te |

Except for the charge controlling agent for use in the present invention, the same components as those employed in conventional toners can be employed in the present invention.

Specific examples of the binder resins include the following homopolymers of styrene and substitution products thereof such as polystyrene, chloropolystyrene and polyvinyltoluene; copolymers of styrene such as styrene-chloropolystyrene copolymer, styrene-propylene copolymer, styrene-vinyltoluene copolymer, styrene-vinylnaphthalene copolymer, styrene-methyl acrylate copolymer, styrene-ethyl acrylate copolymer, styrene-butyl acrylate copolymer, styrene-octyl acrylate copolymer, styrene-methyl methacrylate copolymer, styrene-ethyl methacrylate copolymer, styrene-butyl methacrylate copolymer, styrene-methyl α-chloromethacrylate, styrene-acrylonitrile copolymer, styrene-vinylmethyl ether copolymer, styrene-vinylethyl ether copolymer, styrene-vinylmethyl ketone copolymer, styrene-butadiene copolymer, styrene-isoprene copolymer, styrene-acrylonitrile-indene copolymer, styrene-maleic acid copolymer, and styrene-maleic acid ester copolymer; polymethyl methacrylate, polybutyl methacrylate, polyvinyl chloride, polyvinyl acetate, polyethylene, polypropylene, polyester, polyurethane, polyamide, epoxy resin, polyvinyl butyral, polyacrylic acid resin, rosin, modified rosin, terpene resin, phenolic resin, aliphatic hydrocarbon resin, alicyclic hydrocarbon resin, aromatic petroleum resin, chlorinated paraffin, paraffin wax, and mixtures thereof.

Among the above binder resins, the following resins are so plastic that they are easily deformed under application of pressure, and therefore toners containing such resins exhibit excellent fixing performance when image fixing is performed by application of pressure. For example, polyolefins such as low-molecular-weight-polyethylene, low-molecular-weight-polypropylene, polyethylene oxide and polyethylene tetrafluoride; epoxy resin; polyester resin; styrene-butadiene copolymer (monomer ratio 5 to 30:95 to 70); olefin copolymers such as ethylene-acrylate copolymer, ethylene-acrylic acid ester copolymer, ethylene -methacrylate copolymer, ethylene-methacrylic acid ester copolymer, ethylene-vinyl chloride copolymer, ethylene-vinyl acetate copolymer and ionomer resin; polyvinyl pyrrolidone, methyl vinyl ether-maleic anhydride copolymer, maleic acid modified phenolic resin, phenol modified terpene resin and mixtures thereof are employed.

Examples of the coloring agents for use in the present invention include the following pigments and dyes such as carbon black, lamp black, Oil Black, Azo Oil Black, Sudan Black SM, black iron oxide (magnetite), Fast Yellow C, Benzidine Yellow, Pigment Yellow, Chrome yellow, Quinoline Yellow, Hansa Yellow G, Nigrosine Dye, Indo Fast Orange, Irgasin Red, Para Nitraniline Red, Toluidine Red, Du Pont Oil Red, Rose Bengal, Carmine FE, Permanent Bordeaux FRR, Pigment Orange R, Lithol Red 2G, Lake Red C, Rhodamine FB, Rhodamine E Lake, Methyl Violet E Lake, Phthalocyanine Blue, Pigment Blue, Aniline Blue, chalco oil blue, ultramarine blue, Methylene Blue Chloride, Phthalocyanine Blue, Brilliant Green E, Phthalocyanine Green, Rhodamine 6Lake, Quinacridone, Malachite Green Hexalate, Oil Yellow GG, Zapon Fast Yellow GGG, Kayaset Y963, Kayaset YG, Sumiplast Yellow GG, Zapon Fast Orange RR, Oil Scarlet, Sumiplast Orange, Orazole Brown E, Zapon Fast Scarlet CG, Aizen Spilon Red BEH, Oil Pink OP, azo pigments such as a monoazo pigment, a disazo pigment and a trisazo pigment, a triallyl methane dye, and mixtures thereof.

To the dry-type toner according to the present invention, other auxiliary agents may be added in order to improve or control the thermal, electrical and physical properties, when necessary. For example, there are a plasticizer such as dibutyl phthalate and dioctyl phthalate; a resistance controlling agent or electroconductivity application agent such as tin oxide, lead oxide, antimony oxide and carbon black; a fluidity controlling agent or a caking inhibitor such as colloidal silica and aluminum oxide; an abrasive such as cerium oxide, aluminum oxide, titanium oxide and silicon carbide; a lubricant such as finely-divided particles of fluorine plastics and metallic salts of higher fatty acid, for example, zinc stearate; and fixing promoting agent such as low-molecular-weight polyolefin. Furthermore, a small amount of the conventional charge controlling agents can be added to control the electrical chargeability of the toner.

The dry-type toner according to the present invention is advantageous when used as a two-component type developer by blending this dry-type toner and carrier particles.

Specific examples of the carrier particles for use in the present invention are finely-divided particles of a magnetic material; for example, (a) iron oxides of iron oxide alloys such as magnetite, hematite and ferrite, (b) ferromagnetic metals such as iron, cobalt and nickel, and (c) alloys of ferromagnetic metals and non-metallic metals such as aluminum, copper, lead, magnesium, tin, zinc, antimony, beryllium, bismuth, cadmium, calcium, manganese, selenium, titanium, tungsten and vanadium, and mixtures thereof; glass beads; and previously mentioned finely-divided particles of the magnetic materials and glass beads coated by resins such as styrene-acrylic acid ester copolymer, silicone resin, polyamide resin and ionomer resin. It is preferable that the particle diameter of the above carrier particle be about 40 to 200 $\mu$m (400 to 70 mesh).

The dry-type toner according to the present invention may be used as a one-component type developer by adding thereto the same magnetic material as employed in the preparation for the two-component type developer. The thus obtained one-component type developer is called a magnetic toner. It is preferable that the particle diameter of the magnetic particles be about 0.1 to 2 $\mu$m.

The dry-type toner according to the present invention can be used as a one-component type developer in a development unit as shown in the single figure. In the development unit in the single figure, a toner 6 accumulated in a toner reservoir 7 is forcibly brought onto a sponge roller 4 by a stirring blade 5, so that the toner 6 is supplied onto the sponge roller 4. As the sponge roller 4 is rotated in the direction of the arrow, the toner 6 fed to the sponge roller 4 is transported onto a toner transportation member 2, where the toner 6 is frictioned, and electrostatically or physically attracted to the toner transportation member 2. As the toner transportation member 2 is rotated in the direction of the arrow, a uniformly thin layer of the toner 6 is formed on the toner transportation member 2 by an elastic blade 3. At the same time, the thin layer of the toner 6 is triboelectrically charged. The toner 6 is then transported onto the surface of a latent electrostatic image bearing member 1 which is situated in contact with or adjacent to the toner transportation member 2, so that the latent electrostatic image is developed to a visible toner image.

The dry-type toner according to the present invention can be prepared by conventional methods. In both the one-component type developer and the two-component type developer, the above-mentioned components are kneaded in a roll mill under application of heat, cooled to room temperature, pulverized and classified.

When the dry-type toner according to the present invention is used as two-component type developer, it is preferable that the amount of the coloring agent and the amount of the negative charge controlling agent be respectively in the range of 1 to 30 parts by weight, and 0.1 to 30 parts by weight, to 100 parts by weight of the resin component, in view of the chargeability and fluidity thereof.

When the dry-type toner according to the present invention is used as one-component type developer, the resin, the coloring agent and the negative charge controlling agent may be blended at the same amount ratio as employed in the preparation for the two-component type developer. It is preferable that the amount of the magnetic material for the one-component type developer be in the range of 20 to 200 parts by weight, more preferably in the range of 40 to 150 parts by weight, to 100 parts by weight of the resin component.

Other features of this invention will become apparent in the course of the following description of exemplary embodiments, which are given for illustration of the invention and are not intended to be limiting thereof.

EXAMPLE 1

The following components were mixed in a Henschel mixer and kneaded for about 30 minutes in a roll mill which was heated to 130 to 140° C, whereby a kneaded mixture was obtained. The thus obtained mixture was cooled to room temperature, pulverized and classified, so that a blue toner No. 1 with a particle diameter of 5 to 15 $\mu$m according to the present invention was obtained.

|  | Parts by Weight |
|---|---|
| Styrene-n-butyl methacrylate copolymer | 100 |
| Polypropylene | 5 |
| C.I. Pigment Blue 15 | 5 |
| Metallic salt No. I-(1) | 5 |

3 parts by weight of the above prepared toner No. 1 and 97 parts by weight of silicone-resin-coated ferrite carrier particles having a particle size of 100 to 250 meshes were mixed in a ball mill, whereby a two-component type developer was obtained.

The thus obtained developer was subjected to an image formation test using a commercially available electrophotographic copying machine (Trademark "FT-4060" made by Ricoh Company, Ltd.). The initial images obtained by the above test were clear blue. Even after 200,000 copies were made, the obtained images were still excellent in quality.

The initial charge quantity of the toner, measured by the blow-off method, was $-22.5$ $\mu$C/g. After the making of 200,000 copies, the charge quantity of the toner was $-21.5$ $\mu$C/g, which was almost the same as the initial charge quantity of the toner.

In addition, under the conditions of high humidity of 90% RH at 35° C., and low humidity of 10% RH at 15° C., the image quality of the obtained images was not deteriorated. The film forming of the toner on the photoconductor was not observed.

EXAMPLE 2

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a red toner No. 2 with a particle diameter of 5 to 20 $\mu$m according to the present invention was obtained.

|  | Parts by Weight |
|---|---|
| Styrene - 2-ethylhexyl acrylate copolymer | 100 |
| Polyethylene | 5 |
| C.I. Pigment Red 81 | 5 |
| C.I. Pigment Red 48 | 3 |
| Metallic salt No. I-(2) | 5 |

3 parts by weight of silicon carbide having a particle diameter of about 2 $\mu$m were added to 100 parts by weight of the above prepared toner No. 2 and kneaded in a speed kneader, whereby a one-component type developer was obtained.

The thus obtained developer was subjected to an image formation test using the development unit as shown in the single figure. In this example, an electrical charge of +800 volts d.c. was uniformly applied to a selenium photoconductor 1, the photoconductor 1 was exposed to a light image to form a latent electrostatic image thereon, and the latent electrosatic image is developed to a visible toner image by the above prepared developer.

The initial images obtained by the above test were clear red. Even after 50,000 copies were made, the obtained images were still excellent in quality.

The initial charge quantity Q/M of the toner on the toner transportation member 2 as shown in the single figure, measured by use of a specific charge quantity measuring apparatus, was $-9.3$ $\mu$C/g. In the above specific charge quantity measuring apparatus, the toner particles on the toner transportation member 2 were sucked by a Faraday cage, with a filter layer equipped at an outlet thereof, and trapped therein to measure the charge quantity of the toner. After the making of 50,000 copies, the charge quantity of the toner was $-8.5$ $\mu$C/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 3

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a green toner No. 3 with a particle diameter of 5 to 20 $\mu$m according to the present invention was obtained.

|  | Parts by Weight |
|---|---|
| Epoxy resin | 100 |
| Polypropylene | 5 |
| C.I. Pigment Blue 15 | 2 |
| C.I. Pigment Yellow 17 | 5 |
| Metallic salt No. I-(5) | 3 |

5 parts by weight of the above prepared toner No. 3 and 100 parts by weight of iron powder carrier particles having a particle size of 100 to 200 meshes were mixed in a ball mill, whereby a two-component type developer was obtained.

The thus obtained developer was subjected to the same image formation test as in Example 1. The initial images obtained by the above test were clear green. Even after 200,000 copies were made, the obtained images were still excellent in quality.

The initial charge quantity of the toner, measured by the blow-off method, was $-20.2$ $\mu$C/g. After the making of 200,000 copies, the charge quantity of the toner was $-19.3$ $\mu$C/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 4

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a black toner No. 4 with a particle diameter of 5 to 20 $\mu$m according to the present invention was obtained.

|  | Parts by Weight |
|---|---|
| Unsaturated polyester resin | 100 |
| Carbon black | 10 |
| Metal-containing monoazo dye | 1 |
| Metallic salt No. I-(6) | 5 |

2 parts by weight of silicon carbide having a particle diameter of about 2 $\mu$m and 0.1 part by weight of hydrophobic colloidal silica were added to 100 parts by weight of the above prepared toner No. 4 and kneaded in a speed kneader, whereby a one-component type developer was obtained.

The thus obtained developer was subjected to the same image formation test as in Example 2. The initial images obtained by the above test were clear black.

Even after 50,000 copies were made, the obtained images were still excellent in quality.

The initial charge quantity (Q/M) of the toner on the toner transportation member 2, measured by use of a specific charge quantity measuring apparatus, was $-8.3$ $\mu$C/g. After the making of 50,000 copies, the charge quantity of the toner was $-7.1$ $\mu$C/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLES 5 to 8

The same procedures for the preparation of the toner as in Example 1 were repeated except that the toner composition employed in Example 1 was replaced by the respective toner compositions as shown in Table 1, so that the dry-type toners No. 5 to No. 8 according to the present invention were obtained.

3 parts by weight of each of the toners No. 5 to No. 8 and 97 parts by weight of the respective carrier particles as shown in Table 1 were mixed in a ball mill, whereby two-component type developers were separately obtained.

The thus obtained developers were subjected to the same image formation test as in Example 1. The results are given in Table 1.

Under the conditions of either high humidities or low humidities, the image quality of the obtained images was not deteriorated. The film forming of the toners on the photoconductor was not observed.

TABLE 1

| Example No. | Formulation of Developer | | Image Quality | | Charge Quantity of Toner [$\mu$C/g] | |
|---|---|---|---|---|---|---|
| | Toner Composition | Parts by Weight | Initial Stage | After 200,000 copies | Initial Stage | After 200,000 copies |
| 5. | Polyethylene wax | 50 | Clear black | Almost the same as that in initial stage | $-23.8$ | $-21.8$ |
|  | Ethylene-vinyl acetate copolymer | 20 | | | | |
|  | Magnetite | 40 | | | | |
|  | Metallic salt No. I-(9) | 7 | | | | |
| 6. | Styrene-n-butyl acrylate copolymer | 94 | Clear blue | Same as the above | $-19.5$ | $-18.7$ |
|  | C.I. Pigment Blue 15 | 3 | | | | |
|  | Metallic salt No. I-(11) | 3 | | | | |
|  | Carrier Composition | | | | | |
|  | Carbon-dispersed silicon resin coated ferrite | | | | | |
| 7. | Phenol resin | 10 | Clear black | Same as the above | $-20.1$ | $-19.3$ |
|  | Polyester resin | 68 | | | | |
|  | Polypropylene | 6 | | | | |
|  | Carbon black | 10 | | | | |
|  | Carrier Composition | | | | | |
|  | Iron powder | | | | | |
| 8. | Styrene-butyl acrylate copolymer | 87 | Clear yellow | Same as the above | $-18.8$ | $-17.1$ |
|  | Polyethylene | 5 | | | | |
|  | C.I. Disperse Yellow 33 | 4 | | | | |
|  | Metallic salt No. I-(18) | 4 | | | | |
|  | Carrier Composition | | | | | |
|  | Silicone-resin-coated ferrite | | | | | |

EXAMPLE 9

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a blue toner No. 9 with a particle diameter of 5 to 20 μm according to the present invention was obtained.

|  | Parts by Weight |
| --- | --- |
| Styrene-n-butyl methacrylate | 100 |
| Polypropylene | 5 |
| C.I. Pigment Blue 15 | 5 |
| Metallic salt No. I-(21) | 4 |

2.5 parts by weight of the above prepared toner No. 9 and 97.5 parts by weight of silicone-resin-coated ferrite carrier particles having a particle size of 100 to 250 meshes were mixed in a ball mill, whereby a two-component type developer was obtained.

The thus obtained developer was subjected to the same image formation test as in Example 1. The initial images obtained by the above test were clear blue. Even after 200,000 copies were made, the obtained images were still excellent in quality.

The initial charge quantity of the toner, measured by the blow-off method, was $-20.5$ μC/g. After the making of 200,000 copies, the charge quantity of the toner was $-19.2$ μC/g, which was almost the same as the initial charge quantity of the toner.

In addition, under the conditions of high humidity of 90% RH at 35° C., and low humidity of 15% RH at 10° C., the image quality of the obtained images was not deteriorated. The film forming of the toner on the photoconductor was not observed.

COMPARATIVE EXAMPLE 1

Example 9 was repeated except that 4 parts by weight of the metallic salt No. I-(21) in the formulation of the toner prepared in Example 9 was replaced by 4 parts by weight of a commercially available zinc salicylate (Trademark "E-84" made by Orient Chemical Industries, Ltd.), whereby a comparative two-component type developer was obtained.

The thus obtained comparative two-component developer was subjected to the same image formation test as in Example 1. The initial images obtained by the above test were clear blue and free from fogging. After 100,000 copies were made, the obtained images became unclear with fogging.

The initial charge quantity of the toner, measured by the blow-off method, was $-16.4$ μC/g. After the making of 100,000 copies, the charge quantity of the toner was remarkably decreased to $-4.8$ μC/g.

Under the conditions of high humidity of 90% RH at 35° C., the obtained images became unclear and the image density thereof was as low as 0.95. The film forming of the toner on the photoconductor was observed after the making of 100,000 copies.

EXAMPLE 10

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a red toner No. 10 with a particle diameter of 5 to 20 μm according to the present invention was obtained.

|  | Parts by Weight |
| --- | --- |
| Styrene - 2-ethylhexyl acrylate copolymer | 100 |
| Polypropylene | 5 |
| C.I. Pigment Red 57 | 5 |
| C.I. Pigment Red 48 | 3 |
| Metallic salt No. I-(22) | 3 |

3 parts by weight of silicon carbide having a particle diameter of about 2 μm and 0.1 part by weight of hydrophobic colloidal silica were added to 100 parts by weight of the above prepared toner No. 10 and kneaded in a speed kneader, whereby a one-component type developer was obtained.

The thus obtained developer was subjected to an image formation test using a development unit as shown in the single figure. In this example, $-800$ volts d.c. was uniformly applied to an organic photoconductor 1, and the photoconductor 1 was exposed to a light image to form a latent electrostatic image thereon. By use of the above prepared developer, the latent electrostatic image was subjected to reverse development. The initial images obtained by the above test were clear red. Even after 50,000 copies were made, the obtained images were still excellent in quality.

The initial charge quantity (Q/M) of the toner on the toner transportation member 2, measured by use of a specific charge quantity measuring apparatus, was $-12.1$ μC/g. After the making of 50,000 copies, the charge quantity of the toner was $-9.5$ μC/g, which was almost the same as the initial charge quantity of the toner.

In addition, under the conditions of either high humidities or low humidities, the image quality of the obtained images was not deteriorated. The film forming of the toner on the photoconductor was not observed.

COMPARATIVE EXAMPLE 2

Example 10 was repeated except that 3 parts by weight of the metallic salt No. I-(22) in the formulation of the toner prepared in Example 10 was replaced by 0.5 parts by weight of a commercially available metal-containing monoazo dye (Trademark "S-34" made by Orient Chemical Industries, Ltd.), whereby a comparative one-component type developer was obtained.

The thus obtained comparative one-component developer was subjected to the same image formation test as in Example 2. The initial images obtained by the above test were clear red and free from fogging. After 100,000 copies were made, the obtained images became unclear with fogging.

The initial charge quantity of the toner, measured by the same manner as employed in Example 10, was $-15.1$ μC/g. After the making of 100,000 copies, the charge quantity of the toner was remarkably decreased to $-3.5$ μC/g.

Under the conditions of high humidity of 90% RH at 35° C., the obtained images became unclear and the image density thereof was as low as 0.86.

EXAMPLE 11

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a green toner No. 11 with a particle diameter of 5 to 20 μm according to the present invention was obtained.

|  | Parts by Weight |
|---|---|
| Epoxy resin | 100 |
| Polyethylene | 5 |
| C.I. Pigment Blue 15 | 5 |
| C.I. Pigment Yellow 17 | 5 |
| Metallic salt No. I-(23) | 4 |

3.5 parts by weight of the above prepared toner No. 11 and 96.5 parts by weight of iron powder carrier particles having a particle size of 100 to 200 meshes were mixed in a ball mill, whereby a two-component type developer was obtained.

The thus obtained developer was subjected to the same image formation test as in Example 1. The initial images obtained by the above test were clear green. Even after 200,000 copies were made, the obtained images were still excellent in quality.

The initial charge quantity of the toner, measured by the blow-off method, was −18.5 μC/g. After the making of 200,000 copies, the charge quantity of the toner was −16.9 μC/g, which was almost the same as the initial charge quantity of the toner.

In addition, under the conditions of either high humidity of 90% RH at 35° C., or low humidity of 15% RH at 10° C., the image quality of the obtained images was not deteriorated. The film forming of the toner on the photoconductor was not observed.

EXAMPLE 12

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a black toner No. 12 with a particle diameter of 5 to 25 μm according to the present invention was obtained.

|  | Parts by Weight |
|---|---|
| Unsaturated polyester resin | 100 |
| Polypropylene | 5 |
| Carbon black | 10 |

-continued

|  | Parts by Weight |
|---|---|
| Metallic salt No. I-(25) | 2 |

2.5 parts by weight of silicon carbide having a particle diameter of about 2 μm and 0.1 part by weight of hydrophobic colloidal silica were added to 100 parts by weight of the above prepared toner No. 12 and kneaded in a speed kneader, whereby a one-component type developer was obtained.

The thus obtained developer was subjected to the same image formation test as in Example 10. The initial images obtained by the above test were clear black. Even after 50,000 copies were made, the obtained images were still excellent in quality.

The initial charge quantity (Q/M) of the toner on the toner transportation member 2, measured by use of a specific charge quantity measuring apparatus, was −24.6 μC/g. After the making of 50,000 copies, the charge quantity of the toner was −23.1 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLES 13 to 16

The same procedures for the preparation of the toner as in Example 1 were repeated except that the toner composition employed in Example 9 was replaced by the respective toner compositions as shown in Table 2, so that dry-type toners No. 13 to No. 16 according to the present invention were obtained.

3 parts by weight of each of the toners No. 13 to No. 16 and 97 parts by weight of the respective carrier particles as shown in Table 2 were mixed in a ball mill, whereby two-component type developers were separately obtained.

The thus obtained developers were subjected to the same image formation test as in Example 1. The results are given in Table 2.

Under the conditions of either high humidities or low humidities, the image quality of the obtained images was not deteriorated. The film forming of the toner on the photoconductor was not observed.

TABLE 2

| Example No. | Formulation of Developer | | Image Quality | | Charge Quantity of Toner [μC/g] | |
|---|---|---|---|---|---|---|
| | Toner Composition | Parts by Weight | Initial Stage | After 200,000 copies | Initial Stage | After 200,000 copies |
| 13. | Polyethylene wax | 62 | Clear blue | Almost the same as that in initial stage | −22.8 | −20.5 |
|  | Ethylene-vinyl acetate copolymer | 40 | | | | |
|  | C.I. Pigment Blue 15 | 4 | | | | |
|  | Metallic salt No.I-(27) | 6 | | | | |
|  | Carrier Composition | | | | | |
|  | Silicon-resin-coated ferrite | | | | | |
| 14. | Polyester resin | 75 | Clear black | Same as the above | −21.7 | −19.6 |
|  | Polypropylene | 5 | | | | |
|  | Carbon black | 10 | | | | |
|  | Metallic salt No. I-(29) | 5 | | | | |
|  | Carrier Composition | | | | | |
|  | Finely-divided particles of iron oxide | | | | | |
| 15. | Styrene-n-butyl acrylate copolymer | 80 | Clear yellow | Same as the above | −18.8 | −17.2 |
|  | Polyethylene | 10 | | | | |

TABLE 2-continued

| Example No. | Formulation of Developer — Toner Composition | Parts by Weight | Image Quality — Initial Stage | Image Quality — After 200,000 copies | Charge Quantity of Toner [μC/g] — Initial Stage | Charge Quantity of Toner [μC/g] — After 200,000 copies |
|---|---|---|---|---|---|---|
| | C.I. Disperse Yellow 33 | 5 | | | | |
| | Metallic salt No. I-(31) | 7 | | | | |
| | Carrier Composition | | | | | |
| | Silicone-resin-coated ferrite | | | | | |
| 16. | Styrene-n-butyl acrylate copolymer | 83.5 | Clear green | Same as the above | −17.5 | −16.2 |
| | Polypropylene | 5 | | | | |
| | C.I. Pigment Blue 15 | 5 | | | | |
| | C.I. Pigment Yellow 17 | 3 | | | | |
| | Metallic salt No. I-(34) | 4.5 | | | | |
| | Carrier Composition | | | | | |
| | Finely-divided particles of iron oxide | | | | | |
| 17. | Styrene-n-butyl acrylate copolymer | 80 | Clear blue | Same as the above | −20.2 | −18.5 |
| | Polyethylene | 10 | | | | |
| | C.I. Pigment Blue 15 | 5 | | | | |
| | Metallic salt No. I-(37) | 7 | | | | |
| | Carrier Composition | | | | | |
| | Silicone-resin-coated ferrite | | | | | |

EXAMPLE 17

The same procedures for the preparation of the toner as in Example 1 were repeated except that 5 parts by weight of the metallic salt No. I-[5] was replaced by 4 parts by weight of a metallic salt No. I-(39), so that a blue toner No. 17 with a particle diameter of 5 to 20 μm according to the present invention was obtained.

2.5 parts by weight of the above prepared toner No. 17 and 97.5 parts by weight of finely-divided ferrite carrier particles having a particle size of 100 to 250 meshes were mixed in a ball mill, whereby a two-component type developer was obtained.

The thus obtained developer was subjected to the same image formation test as in Example 1. The initial images obtained by the above test were clear blue. Even after 200,000 copies were made, the obtained images were still excellent in quality.

The initial charge quantity of the toner, measured by the blow-off method, was −20.5 μC/g. After the making of 200,000 copies, the charge quantity of the toner was −19.2 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 18

The following components were mixed in a Henschel mixer and kneaded for about 30 minutes in a roll mill which was heated to 130 to 140° C., whereby a kneaded mixture was obtained. The thus obtained mixture was cooled to room temperature, pulverized and classified, so that a red toner No. 18 with a particle diameter of 5 to 20 μm according to the present invention was obtained.

| | Parts by Weight |
|---|---|
| Styrene - 2-ethylhexyl acrylate copolymer | 100 |
| Polypropylene | 5 |
| C.I. Pigment Red 57 | 5 |
| C.I. Pigment Red 48 | 3 |
| Metallic salt No. I-(40) | 3 |

3 parts by weight of silicon carbide having a particle diameter of about 2 μm and 0.1 part by weight of hydrophobic colloidal silica were added to 100 parts by weight of the above prepared toner No. 18 and kneaded in a speed kneader, whereby a one-component type developer was obtained.

The thus obtained developer was subjected to the same image formation test as in Example 10. The initial images obtained by the above test were clear red. Even after 50,000 copies were made, the obtained images were still excellent in quality.

The initial charge quantity (Q/M) of the toner on the toner transportation member 2, measured by use of a specific charge quantity measuring apparatus in the same manner as employed in Example 2, was −12.1 μC/g. After the making of 50,000 copies, the charge quantity of the toner was −9.5 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 19

The same procedures for the preparation of the toner as in Example 3 were repeated except that 3 parts by weight of the metallic salt No. I-(5) was replaced by 4 parts by weight of a metallic salt No. I-(41) and 5 parts by weight of polypropylene was replaced by 5 parts by weight of polyethylene, so that a green toner No. 19 with a particle diameter of 5 to 20 μm according to the present invention was obtained.

3.5 parts by weight of the above prepared toner No. 19 and 96.5 parts by weight of finely-divided ferrite carrier particles having a particle size of 100 to 200 meshes were mixed in a ball mill, whereby a two-component type developer was obtained.

The thus obtained developer was subjected to the same image formation test as in Example 1. The initial images obtained by the above test were clear green. Even after 200,000 copies were made, the obtained images were still excellent in quality.

The initial charge quantity of the toner, measured by the blow-off method, was −18.5 μC/g. After the making of 200,000 copies, the charge quantity of the toner was −16.9 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 20

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a black toner No. 20 with a particle diameter of 5 to 25 μm according to the present invention was obtained.

|  | Parts by Weight |
|---|---|
| Unsaturated polyester resin | 100 |
| Polypropylene | 5 |
| Carbon black | 10 |
| Metallic salt No. I-(43) | 2 |

2 parts by weight of silicon carbide having a particle diameter of about 2 μm and 0.1 part by weight of hydrophobic colloidal silica were added to 100 parts by weight of the above prepared toner No. 20 and kneaded in a speed kneader, whereby a one-component type developer was obtained.

The thus obtained developer was subjected to the same image formation test as in Example 2. The initial images obtained by the above test were clear black. Even after 50,000 copies were made, the obtained images were still excellent in quality.

The initial charge quantity (Q/M) of the toner on the toner transportation member 2, measured by use of a specific charge quantity measuring apparatus, was −24.6 μC/g. After the making of 50,000 copies, the charge quantity of the toner was −23.1 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLES 21 to 25

The same procedures for the preparation of the toner as in Example 1 were repeated except that the toner composition employed in Example 1 was replaced by the respective toner compositions as shown in Table 3, so that dry-type toners No. 21 to No. 25 according to the present invention were obtained.

3 parts by weight of each of the toners No. 21 to No. and 97 parts by weight of the respective carrier particles as shown in Table 3 were mixed in a ball mill, whereby two-component type developers were separately obtained.

The thus obtained developers were subjected to the same image formation test as in Example 1. The results are given in Table 3.

Under the conditions of either high humidities or low humidities, the image quality of the obtained images was not deteriorated. The film forming of the toner on the photoconductor was not observed.

TABLE 3

| Example No. | Formulation of Developer | Parts by Weight | Image Quality Initial Stage | Image Quality After 200,000 copies | Charge Quantity of Toner [μC/g] Initial Stage | Charge Quantity of Toner [μC/g] After 200,000 copies |
|---|---|---|---|---|---|---|
| 21. | Toner Composition | | Clear blue | Almost the same as that in initial stage | −22.8 | −20.5 |
|  | Polyethylene wax | 62 | | | | |
|  | Ethylene-vinyl acetate copolymer | 40 | | | | |
|  | C.I. Pigment Blue 15 | 4 | | | | |
|  | Metallic salt No. I-(45) | 6 | | | | |
|  | Carrier Composition | | | | | |
|  | Silicon-resin-coated ferrite | | | | | |
| 22. | Toner Composition | | Clear black | Same as the above | −21.7 | −19.6 |
|  | Polyester resin | 75 | | | | |
|  | Polypropylene | 5 | | | | |
|  | Carbon black | 10 | | | | |
|  | Metallic salt No. I-(47) | 5 | | | | |
|  | Carrier Composition | | | | | |
|  | Finely-divided particles of iron oxide | | | | | |
| 23. | Toner Composition | | Clear yellow | Same as the above | −18.8 | −17.2 |
|  | Styrene-n-butyl acrylate copolymer | 80 | | | | |
|  | Polyethylene | 10 | | | | |
|  | C.I. Disperse Yellow 33 | 5 | | | | |
|  | Metallic salt No. I-(49) | 7 | | | | |
|  | Carrier Composition | | | | | |
|  | Silicone-resin-coated ferrite | | | | | |
| 24. | Toner Composition | | Clear green | Same as the | −17.5 | −16.2 |
|  | Styrene-n-butyl acrylate copolymer | 83.5 | | | | |

TABLE 3-continued

| Example No. | Formulation of Developer | Parts by Weight | Image Quality Initial Stage | Image Quality After 200,000 copies | Charge Quantity of Toner [μC/g] Initial Stage | Charge Quantity of Toner [μC/g] After 200,000 copies |
|---|---|---|---|---|---|---|
| | Polypropylene | 5 | | above | | |
| | C.I. Pigment Blue 15 | 5 | | | | |
| | C.I. Pigment Yellow 17 | 3 | | | | |
| | Metallic salt No. I-(52) | 4.5 | | | | |
| | Carrier Composition | | | | | |
| | Finely-divided particles of iron oxide | | | | | |
| 25. | Toner Composition | | | | | |
| | Styrene-n-butyl acrylate copolymer | 80 | Clear blue | Same as the above | −20.2 | −18.5 |
| | Polyethylene | 10 | | | | |
| | C.I. Pigment Blue 15 | 5 | | | | |
| | Metallic salt No. I-(55) | 7 | | | | |
| | Carrier Composition | | | | | |
| | Silicone-resin-coated ferrite | | | | | |

EXAMPLE 26

The same procedures for the preparation of the toner as in Example 1 were repeated except that 5 parts by weight of the metallic salt No. I-(5) was replaced by 5 parts by weight of a metallic salt No. II-(1), so that a blue toner No. 26 with a particle diameter of 5 to 15 μm according to the present invention was obtained.

3 parts by weight of the above prepared toner No. 26 and 97 parts by weight of finely-divided polymethylmethacrylate-coated ferrite carrier particles having a particle size of 100 to 250 meshes were mixed in a ball mill, whereby a two-component type developer was obtained.

The thus obtained developer was subjected to the same image formation test as in Example 1. The initial images obtained by the above test were clear blue. Even after 200,000 copies were made, the obtained images were still excellent in quality.

The initial charge quantity of the toner, measured by the blow-off method, was −20.5 μC/g. After the making of 200,000 copies, the charge quantity of the toner was 19.8 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 27

The same procedures for the preparation of the toner as in Example 2 were repeated except that 5 parts by weight of the metallic salt No. I-(2) was replaced by 3 parts by weight of a metallic salt No. II-(3), so that a red toner No. 27 with a particle diameter of 5 to 15 μm according to the present invention was obtained.

3 parts by weight of silicon carbide having a particle diameter of about 2 μm were added to 100 parts by weight of the above prepared toner No. 27 and kneaded in a speed kneader, whereby a one-component type developer was obtained.

The thus obtained developer was subjected to the same image formation test as in Example 2. The initial images obtained by the above test were clear red. Even after 50,000 copies were made, the obtained images were still excellent in quality.

The initial charge quantity (Q/M) of the toner on the toner transportation member 2, measured by use of a specific charge quantity measuring apparatus, was −8.5 μC/g. After the making of 50,000 copies, the charge quantity of the toner was −7.6 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 28

The same procedures for the preparation of the toner as in Example 3 were repeated except that 3 parts by weight of the metallic salt No. I-(5) was replaced by 2 parts by weight of a metallic salt No. II-(6), so that a green toner No. 28 with a particle diameter of 5 to 20 μm according to the present invention was obtained.

5 parts by weight of the above prepared toner No. 28 and 100 parts by weight of iron powder carrier particles having a particle size of 100 to 200 meshes were mixed in a ball mill, whereby a two-component type developer was obtained.

The thus obtained developer was subjected to the same image formation test as in Example 1. The initial images obtained by the above test were clear green. Even after 200,000 copies were made, the obtained images were still excellent in quality.

The initial charge quantity of the toner, measured by the blow-off method, was −17.8 μC/g. After the making of 200,000 copies, the charge quantity of the toner was −17.3 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 29

The same procedures for the preparation of the toner as in Example 4 were repeated except that 5 parts by weight of the metallic salt No. I-(6) was replaced by 5 parts by weight of a metallic salt No. II-(5), and the amount of the metal-containing monoazo dye was increased to 2 parts by weight, so that a black toner No. 29 with a particle diameter of 5 to 20 μm according to the present invention was obtained.

2 parts by weight of silicon carbide having a particle diameter of about 2 μm and 0.1 part by weight of hydrophobic colloidal silica were added to 100 parts by weight of the above prepared toner No. 29 and kneaded in a speed kneader, whereby a one-component type developer was obtained.

The thus obtained developer was subjected to the same image formation test as in Example 2. The initial images obtained by the above test were clear black.

whereby two-component type developers were separately obtained.

The thus obtained developers were subjected to the same image formation test as in Example 1. The results are given in Table 4.

Under the conditions of either high humidities or low humidities, the image quality of the obtained images was not deteriorated. The film forming of the toner on the photoconductor was not observed.

TABLE 4

| Example No. | Formulation of Developer | Parts by Weight | Image Quality Initial Stage | Image Quality After 200,000 copies | Charge Quantity of Toner [μC/g] Initial Stage | Charge Quantity of Toner [μC/g] After 200,000 copies |
|---|---|---|---|---|---|---|
| 30. | Toner Composition | | Clear black | Almost the same as that in initial stage | −19.3 | −18.5 |
| | Polyethylene wax | 50 | | | | |
| | Ethylene-vinyl acetate copolymer | 20 | | | | |
| | Magnetite | 40 | | | | |
| | Metallic salt No. II-(9) | 2 | | | | |
| 31. | Toner Composition | | Clear blue | Same as the above | −18.2 | −17.8 |
| | Styrene-n-butyl acrylate copolymer | 87 | | | | |
| | C.I. Pigment Blue 15 | 7 | | | | |
| | Metallic salt No. II-(11) | 6 | | | | |
| | Carrier Composition | | | | | |
| | Carbon-dispersed silicon resin coated ferrite | | | | | |
| 32. | Toner Conposition | | Clear black | Same as the above | −21.3 | −20.5 |
| | Phenol resin | 10 | | | | |
| | Polyester resin | 70 | | | | |
| | Polypropylene | 5 | | | | |
| | Carbon black | 10 | | | | |
| | Metallic salt No. II-(13) | 5 | | | | |
| | Carrier Composition | | | | | |
| | Iron powder | | | | | |
| 33. | Toner Composition | | Clear yellow | Same as the above | −20.1 | −19.4 |
| | Styrene-butyl acrylate copolymer | 86 | | | | |
| | Polyethylene | 6 | | | | |
| | C.I. Disperse Yellow 33 | 4 | | | | |
| | Metallic salt No. II-(18) | 4 | | | | |
| | Carrier Composition | | | | | |
| | Polymethyl-methacrylate-coated ferrite | | | | | |

Even after 50,000 copies were made, the obtained images were still excellent in quality.

The initial charge quantity (Q/M) of the toner on the toner transportation member 2, measured by use of a specific charge quantity measuring apparatus, was −12.1 μC/g. After the making of 50,000 copies, the charge quantity of the toner was −10.9 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLES 30 to 33

The same procedures for the preparation of the toner as in Example 1 were repeated except that the toner composition employed in Example 1 was replaced by the respective toner compositions as shown in Table 4, so that dry-type toners No. 30 to No. 33 according to the present invention were obtained.

3 parts by weight of each of the toners No. 30 to No. 33 and 97 parts by weight of the respective carrier particles as shown in Table 4 were mixed in a ball mill,

EXAMPLE 34

The same procedures for the preparation of the toner as in Example 1 were repeated except that 5 parts by weight of the metallic salt No. I-(1) was replaced by 3 parts by weight of a metallic salt No. III-(1), so that a blue toner No. 34 with a particle diameter of 5 to 15 μm according to the present invention was obtained.

2.5 parts by weight of the above prepared toner No. 34 and 97.5 parts by weight of the same finely-divided silicone-resin-coated carrier particles as that employed in Example 1 were mixed in a ball mill, whereby a two-component type developer was obtained.

The thus obtained developer was subjected to the same image formation test as in Example 1. The initial images obtained by the above test were clear blue. Even after 200,000 copies were made, the obtained images were still excellent in quality.

The initial charge quantity of the toner, measured by the blow-off method, was −16.2 μC/g. After the making of 200,000 copies, the charge quantity of the toner was −15.1 μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 35

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a red toner No. 35 with a particle diameter of 5 to 20 μm according to the present invention was obtained.

|  | Parts by Weight |
| --- | --- |
| Styrene - 2-ethylhexyl acrylate copolymer | 100 |
| Polypropylene | 5 |
| C.I. Pigment Red 57 | 5 |
| C.I. Pigment Red 48 | 3 |
| Metallic salt No. III-(2) | 5 |

3 parts by weight of silicon carbide having a particle diameter of about 2 μm and 0.1 part by weight of hydrophobic colloidal silica were added to 100 parts by weight of the above prepared toner No. 35 and kneaded in a speed kneader, whereby a one-component type developer was obtained.

The thus obtained developer was subjected to the same image formation test as in Example 2. The initial images obtained by the above test were clear red. Even after 50,000 copies were made, the obtained images were still excellent in quality.

The initial charge quantity (Q/M) of the toner on the toner transportation member 2, measured by use of a specific charge quantity measuring apparatus in the same manner as employed in Example 2, was $-10.2$ μC/g. After the making of 50,000 copies, the charge quantity of the toner was $-8.6$ μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 36

The following components were mixed in a Henschel mixer and kneaded for about 30 minutes in a roll mill which was heated to 130° to 140° C., whereby a kneaded mixture was obtained. The thus obtained mixture was cooled to room temperature, pulverized and classified, so that a green toner No. 36 with a particle diameter of 5 to 20 μm according to the present invention was obtained.

|  | Parts by Weight |
| --- | --- |
| Epoxy resin | 100 |
| Polyethylene | 5 |
| C.I. Pigment Blue 15 | 5 |
| C.I. Pigment Yellow 17 | 5 |
| Metallic salt No. III-(5) | 4 |

3.5 parts by weight of the above prepared toner No. 36 and 96.5 parts by weight of iron powder carrier particles having a particle size of 100 to 200 meshes were mixed in a ball mill, whereby a two-component type developer was obtained.

The thus obtained developer was subjected to the same image formation test as in Example 1. The initial images obtained by the above test were clear green. Even after 200,000 copies were made, the obtained images were still excellent in quality.

The initial charge quantity of the toner, measured by the blow-off method, was $-17.8$ μC/g. After the making of 200,000 copies, the charge quantity of the toner was $-16.2$ μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLE 37

The following components were mixed in a Henschel mixer and kneaded for about 30 minutes in a roll mill which was heated to 130° to 140° C., whereby a kneaded mixture was obtained. The thus obtained mixture was cooled to rom temperature, pulverized and classified, so that a black toner No. 37 with a particle diameter of 5 to 25 μm according to the present invention was obtained.

|  | Parts by Weight |
| --- | --- |
| Unsaturated polyester resin | 100 |
| Polypropylene | 5 |
| Carbon black | 10 |
| Metallic salt No. III-(6) | 2.5 |

2.5 parts by weight of silicon carbide having a particle diameter of about 2 μm and 0.1 part by weight of hydrophobic colloidal silica were added to 100 parts b weight of the above prepared toner No. 37 and kneaded in a speed kneader, whereby a one-component type developer was obtained.

The thus obtained developer was subjected to the same image formation test as in Example 2. The initial images obtained by the above test were clear black. Even after 50,000 copies were made, the obtained images were still excellent in quality.

The initial charge quantity (Q/M) of the toner on the toner transportation member 2, measured by use of a specific charge quantity measuring apparatus, was $-9.5$ μC/g. After the making of 50,000 copies, the charge quantity of the toner was $-8.8$ μC/g, which was almost the same as the initial charge quantity of the toner.

In addition, under the conditions of either high humidities or low humidities, the image quality of the obtained images was not deteriorated. The film forming of the toner on the photoconductor was not observed.

EXAMPLES 38 to 41

The same procedures for the preparation of the toner as in Example 1 were repeated except that the toner composition employed in Example 1 was replaced by the respective toner compositions as shown in Table 5, so that dry-type toners No. 38 to No. 41 according to the present invention were obtained.

3 parts by weight of each of the toners No. 38 to No. 41 and 97 parts by weight of the respective carrier particles as shown in Table 5 were mixed in a ball mill, whereby two-component type developers were separately obtained.

The thus obtained developers were subjected to the same image formation test as in Example 1. The results are given in Table 5.

Under the conditions of either high humidities or low humidities, the image quality of the obtained images was not deteriorated. The film forming of the toner on the photoconductor was not observed.

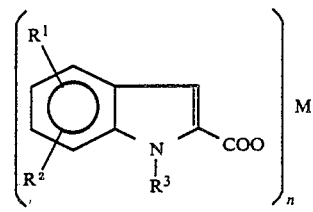

TABLE 5

| Example No. | Formulation of Developer | Parts by Weight | Image Quality Initial Stage | Image Quality After 200,000 copies | Charge Quantity of Toner [μC/g] Initial Stage | Charge Quantity of Toner [μC/g] After 200,000 copies |
|---|---|---|---|---|---|---|
| 38. | Toner Composition | | Clear | Almost the same as that in initial stage | −21.2 | −19.3 |
| | Polyethylene wax | 62 | | | | |
| | Ethylene-vinyl acetate copolymer | 40 | blue | | | |
| | C.I. Pigment Blue 15 | 4 | | | | |
| | Metallic salt No. III-(9) | 8 | | | | |
| | Composition | | | | | |
| | Silicon-resin-coated ferrite | | | | | |
| 39. | Toner Composition | | Clear black | Same as the above | −18.2 | −17.1 |
| | Polyester resin | 75 | | | | |
| | Polypropylene | 5 | | | | |
| | Carbon black | 10 | | | | |
| | Metallic salt No. III-(11) | 10 | | | | |
| | Carrier Composition | | | | | |
| | Finely-divided particles of iron oxide | | | | | |
| 40. | Toner Composition | | Clear yellow | Same as the above | −22.5 | −20.8 |
| | Styrene-n-butyl acrylate copolymer | 80 | | | | |
| | Polyethylene | 10 | | | | |
| | C.I. Disperse Yellow 33 | 5 | | | | |
| | Metallic salt No. III-(13) | 7 | | | | |
| | Carrier Composition | | | | | |
| | Silicone-resin-coated ferrite | | | | | |
| 41. | Toner Composition | | Clear green | Same as the above | −17.7 | −15.6 |
| | Styrene-n-butyl acrylate copolymer | 83.5 | | | | |
| | Polypropylene | 5 | | | | |
| | C.I. Pigment Blue 15 | 5 | | | | |
| | C.I. Pigment Yellow 17 | 3 | | | | |
| | Metallic salt No. III-(17) | 4.5 | | | | |
| | Carrier Composition | | | | | |
| | Finely-divided particles of iron oxide | | | | | |

The toners for developing a latent electrostatic image according to the present invention comprise as the negative charge controlling agent any of the above-mentioned metallic salts, so that the toners have the following advantages over conventional toners:

(1) Triboelectric charge having a negative polarity can be steadily applied to the toner.
(2) The negative charge controlling agent does not fall off the toner, so that the surface of the photoconductor is not stained therewith.
(3) The obtained images, in particular, color images are remarkably clear, and a high image quality is maintained in the course of repeated operation.

What is claimed is:

1. A dry-type toner comprising as the main components a resin component, a coloring agent and a negative charge controlling agent in an effective amount which is selected from the group consisting of:
(i) a metallic salt of indolecarboxylic acid having the formula (I):

wherein $R^1$ and $R^2$, which may be the same or different, each represent hydrogen, a halogen, a nitro group, a carboxy ester group, a hydroxyl group, a sulfonamide group, a cyano group, an alkyl group having 1 to 8 carbon atoms, or an alkoxyl group having 1 to 8 carbon atoms; $R^3$ represents hydrogen or an alkyl group having 1 to 8 carbon atoms; M represents a metal element selected from the group consisting of Zn, Co, Ni, Fe, Cr, Al and Te; and n is a number equivalent to the valence number of the metal represented by M;

(ii) a metallic salt of quinolinecarboxylic acid having the formula (II):

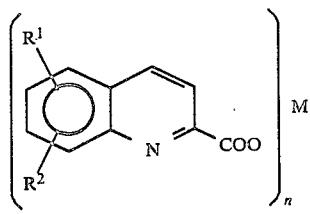

wherein $R^1$, $R^2$, M and n are respectively the same as previously defined in formula (I); and (iii) a metallic salt of benzothiazole derivatives having the formula (III):

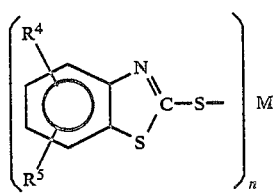

wherein $R^4$ and $R^5$, which may be the same or different, each represent hydrogen, an alkyl group having 1 to 10 carbon atoms, an amino group having 1 to 10 carbon atoms or an alkylamino group having 1 to 10 carbon atoms; M represents a metal element selected from the group consisting of Zn, Co, Ni, Fe and Te; and n is a number equivalent to the valence number of the metal represented by M.

2. The dry-type toner as claimed in claim 1, wherein said negative charge controlling agent is a metallic salt of indolecarboxylic acid having the formula (I):

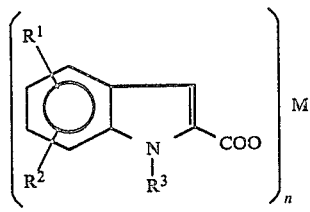

wherein $R^1$ and $R^2$, which may be the same or different, each represent hydrogen, a halogen, a nitro group, a carboxy ester group, a hydroxyl group, a sulfonamide group, a cyano group, an alkyl group having 1 to 8 carbon atoms, or an alkoxyl group having 1 to 8 carbon atoms; $R^3$ represents hydrogen or an alkyl group having 1 to 8 carbon atoms; M represents a metal element selected from the group consisting of Zn, Co, Ni, Fe, Cr, Al and Te; and n is a number equivalent to the valence number of the metal represented by M.

3. The dry-type toner as claimed in claim 1, wherein said negative charge controlling agent is a metallic salt of quinolinecarboxylic acid having the formula [II]:

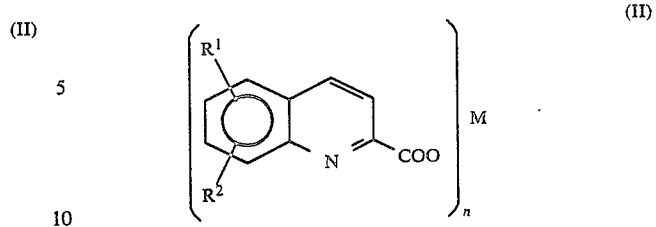

wherein $R^1$ and $R^2$, which may be the same or different, each represent hydrogen, a halogen, a nitro group, a carboxy ester group, a hydroxyl group, a sulfonamide group, a cyano group, an alkyl group having 1 to 8 carbon atoms, or an alkoxyl group having 1 to 8 carbon atoms; M represents a metal element selected from the group consisting of Zn, Co, Ni, Fe, Cr, Al and Te; and n is a number equivalent to the valence number of the metal represented by M.

4. The dry-type toner as claimed in claim 1, wherein said negative charge controlling agent is a metallic salt of benzothiazole derivatives having the formula (III):

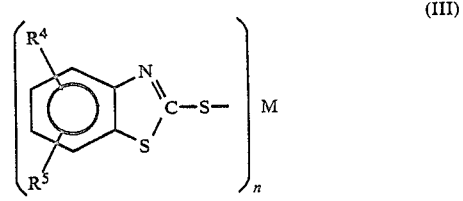

wherein $R^4$ and $R^5$, which may be the same or different, each represent hydrogen, an alkyl group having 1 to 10 carbon atoms, an amino group having 1 to 10 carbon atoms or an alkylamino group having 1 to 10 carbon atoms; M represents a metal element selected from the group consisting of Zn, Co, Ni, Fe and Te; and n is a number equivalent to the valence number of the metal represented by M.

5. The dry-type toner as claimed in claim 2, wherein said metallic salt of idolecarboxylic acid having the general formula (I) is selected from the group consisting of:

| Metallic Salt No. | Chemical Formula |
|---|---|
| I-(1) | 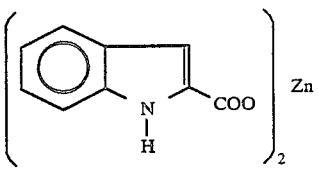 |
| I-(2) | 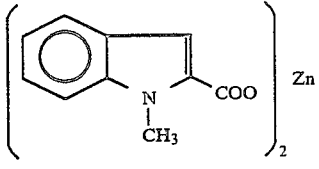 |

| Metallic Salt No. | Chemical Formula |
|---|---|
| I-(3) | 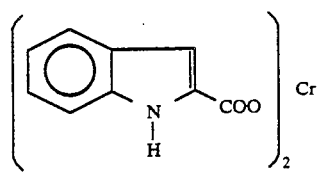 Cr |
| I-(4) | 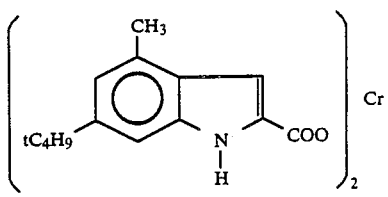 Zn |
| I-(5) | 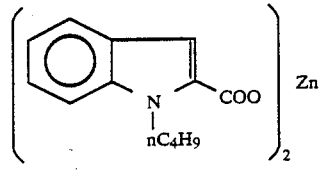 Zn |
| I-(6) | 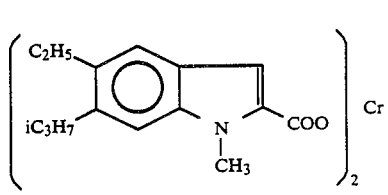 Cr |
| I-(7) | 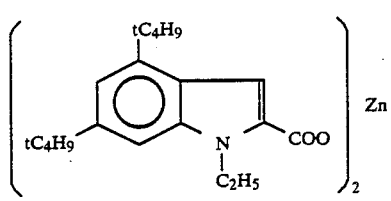 Zn |
| I-(8) | 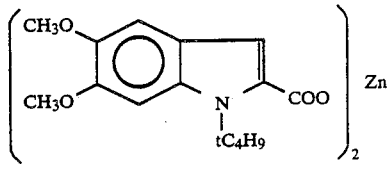 Co |
| I-(9) | 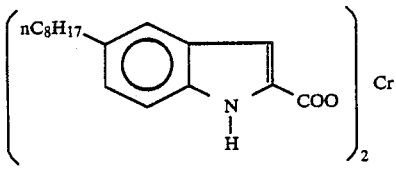 Ni |
| I-(10) | 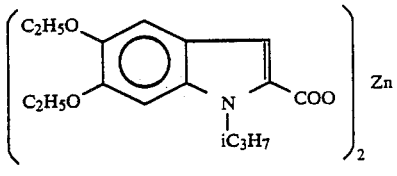 Fe |
| I-(11) | 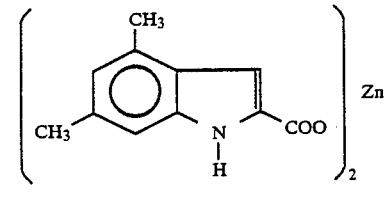 Cr |
| I-(12) | 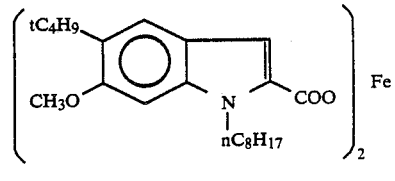 Cr |
| I-(13) | 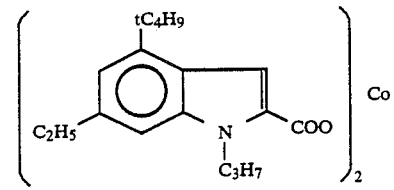 Zn |
| I-(14) | 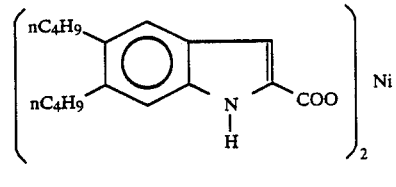 Zn |
| I-(15) | 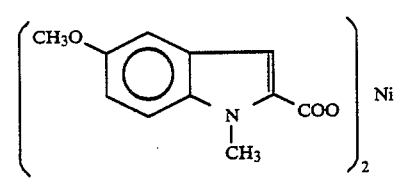 Fe |
| I-(16) | 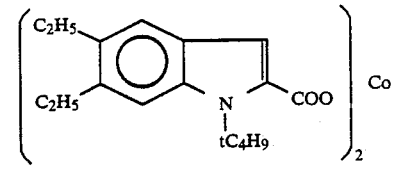 Ni |
| I-(17) | 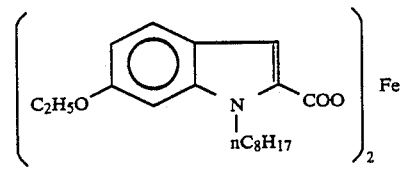 Co |
| I-(18) | 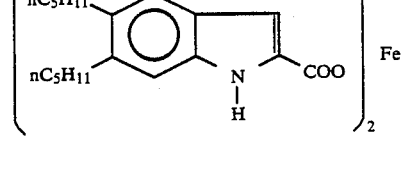 Fe |

-continued
| Metallic Salt No. | Chemical Formula |
|---|---|
| I-(19) | 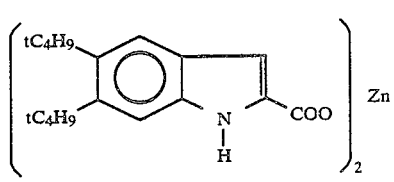 |
| I-(20) | 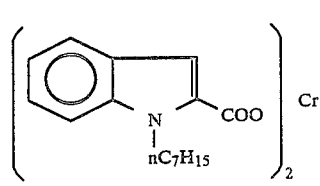 |
| I-(21) | 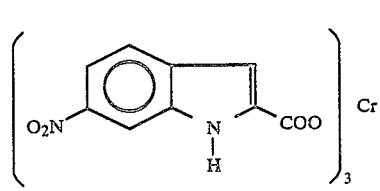 |
| I-(22) | 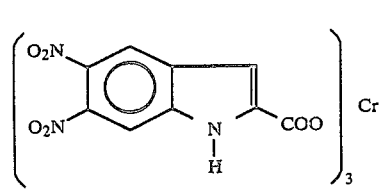 |
| I-(23) | 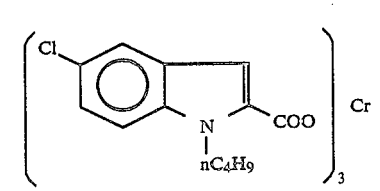 |
| I-(24) | 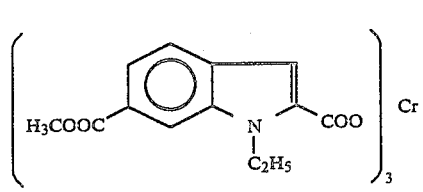 |
| I-(25) | 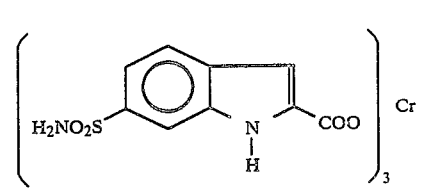 |
| I-(26) | 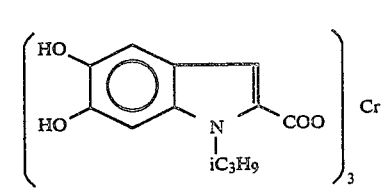 |
-continued
| Metallic Salt No. | Chemical Formula |
|---|---|
| I-(27) | 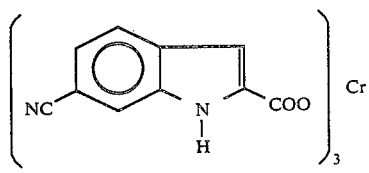 |
| I-(28) | 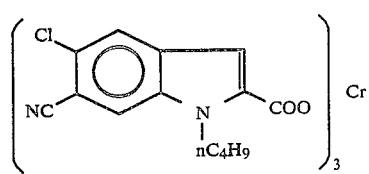 |
| I-(29) | 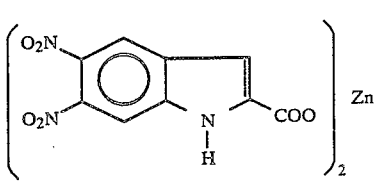 |
| I-(30) | 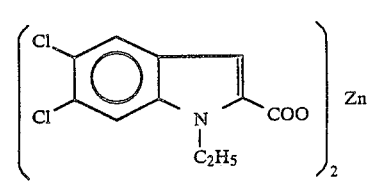 |
| I-(31) | 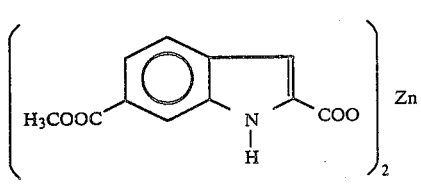 |
| I-(32) | 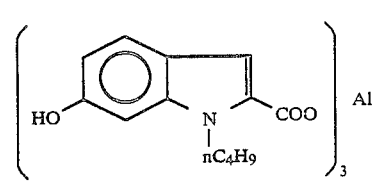 |
| I-(33) | 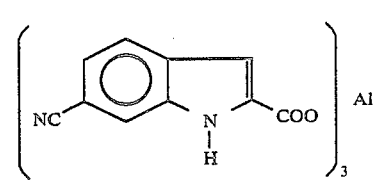 |
| I-(34) | 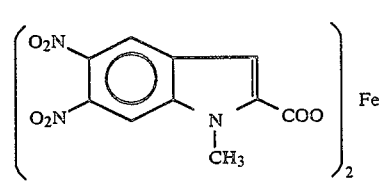 |

| Metallic Salt No. | Chemical Formula |
|---|---|
| I-(35) | 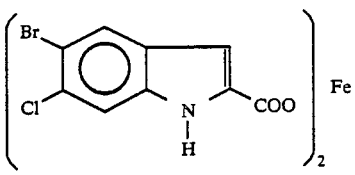 |
| I-(36) | 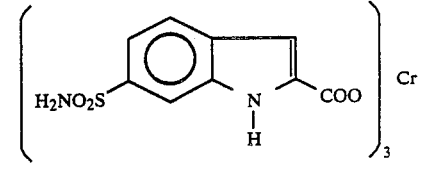 |
| I-(37) | 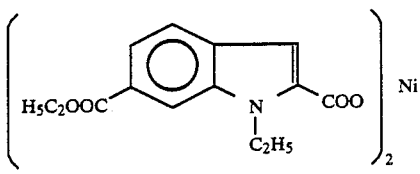 |
| I-(38) | 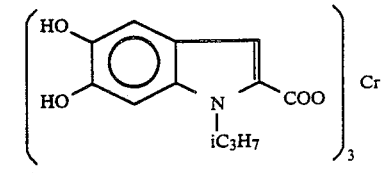 |
| I-(39) | 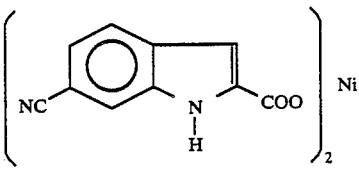 |
| I-(40) | 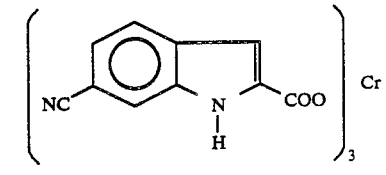 |
| I-(41) | 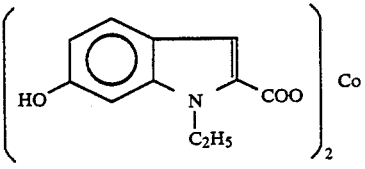 |
| I-(42) | 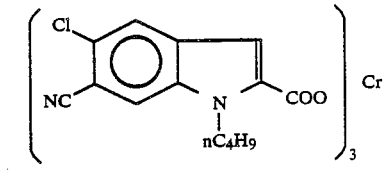 |
| I-(43) | 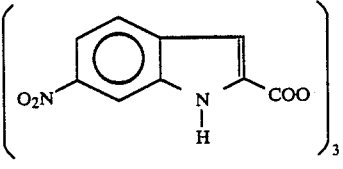 |
| I-(44) | 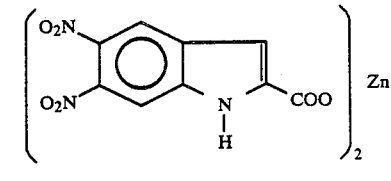 |
| I-(45) | 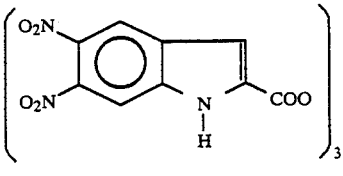 |
| I-(46) | 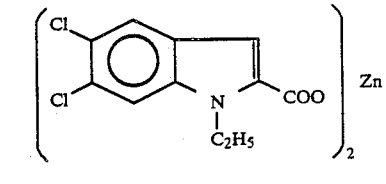 |
| I-(47) | 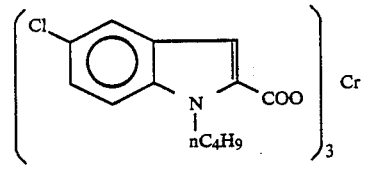 |
| I-(48) | 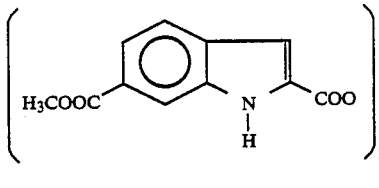 |
| I-(49) | 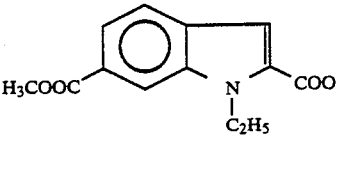 |
| I-(50) | 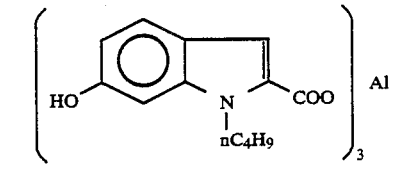 |

| Metallic Salt No. | Chemical Formula |
|---|---|
| I-(51) | 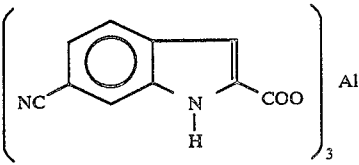 |
| I-(52) | 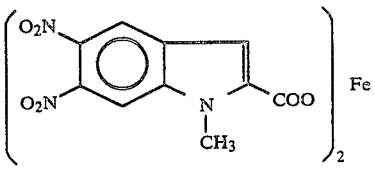 |
| I-(53) | 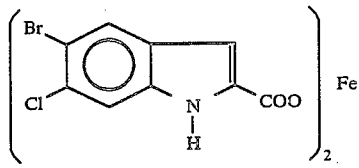 |
| I-(54) | 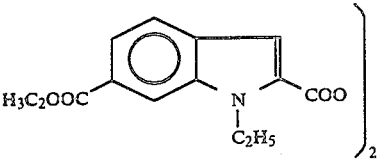 |
| I-(55) | 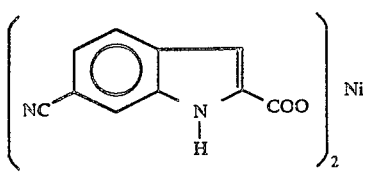 |
| I-(56) | 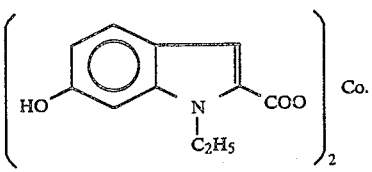 |
6. The dry-type toner as claimed in claim 3, wherein said metallic salt of quinolinecarboxylic acid having the general formula (II) is selected from the group consisting of:
| Metallic Salt No. | Chemical Formula |
|---|---|
| II-(1) | 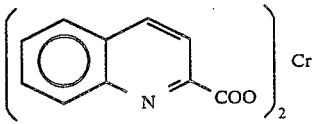 |
| II-(2) | 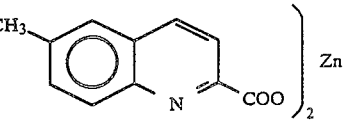 |
| II-(3) | 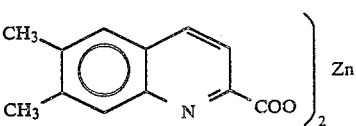 |
| II-(4) | 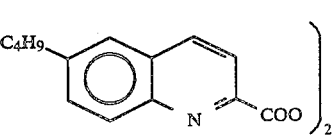 |
| II-(5) | 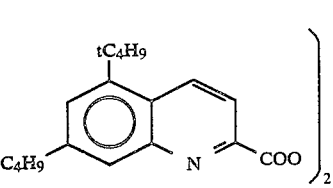 |
| II-(6) | 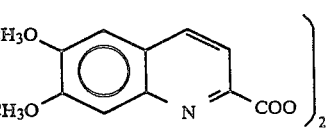 |
| II-(7) | 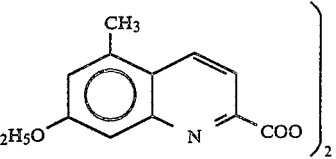 |
| II-(8) | 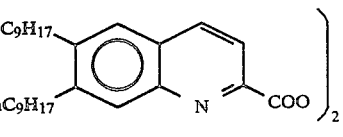 |
| II-(9) | 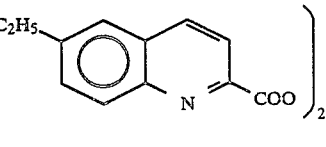 |
| II-(10) | 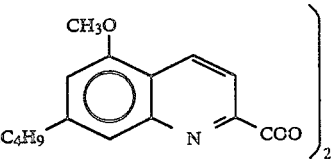 |
| II-(11) | 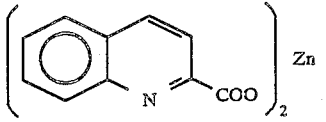 |

| Metallic Salt No. | Chemical Formula |
|---|---|
| II-(12) | [3,4-dimethyl quinoline-2-carboxylate]$_2$ Cr |
| II-(13) | [7-tC$_4$H$_9$ quinoline-2-carboxylate]$_2$ Co |
| II-(14) | [6,7-di-iC$_3$H$_7$ quinoline-2-carboxylate]$_2$ Co |
| II-(15) | [4-CH$_3$O, 7-nC$_7$H$_{15}$ quinoline-2-carboxylate]$_2$ Ni |
| II-(16) | [5,7-di-nC$_8$H$_{17}$ quinoline-2-carboxylate]$_2$ Ni |
| II-(17) | [5,7-di-C$_2$H$_5$ quinoline-2-carboxylate]$_2$ Fe |
| II-(18) | [4-CH$_3$O, 6-CH$_3$ quinoline-2-carboxylate]$_2$ Fe |

7. The dry-type toner as claimed in claim 4, wherein said metallic salt of benzothiazole derivatives having the general formula (III) is selected from the group consisting of:

| Metallic Salt No. | Chemical Formula |
|---|---|
| III-(1) | [benzothiazole-2-thiolate]$_2$ Zn |
| III-(2) | [benzothiazole-2-thiolate]$_2$ Ni |
| III-(3) | [benzothiazole-2-thiolate]$_2$ Co |
| III-(4) | [benzothiazole-2-thiolate]$_2$ Fe |
| III-(5) | [benzothiazole-2-thiolate]$_4$ Te |
| III-(6) | [4-NH$_2$ benzothiazole-2-thiolate]$_2$ Zn |
| III-(7) | [5,6-dimethyl benzothiazole-2-thiolate]$_2$ Zn |
| III-(8) | [5,6-diethyl benzothiazole-2-thiolate]$_2$ Ni |
| III-(9) | [4-CH$_3$ benzothiazole-2-thiolate]$_2$ Fe |
| III-(10) | [4,7-di-nC$_4$H$_9$ benzothiazole-2-thiolate]$_2$ Co |
| III-(11) | [4-NH$_2$ benzothiazole-2-thiolate]$_2$ Co |

-continued

| Metallic Salt No. | Chemical Formula |
|---|---|
| III-(12) | $\left\{\begin{array}{c}\text{benzothiazole with } CH_3 \text{ at 4-position and } H_3C_2 \text{ at 6-position, } C=S-\end{array}\right\}_2 Zn$ |
| III-(13) | $\left\{\begin{array}{c}\text{benzothiazole with } CH_3, C=S-\end{array}\right\}_4 Te$ |
| III-(14) | $\left\{\begin{array}{c}\text{benzothiazole with } tC_4H_9, C=S-\end{array}\right\}_2 Fe$ |
| III-(15) | $\left\{\begin{array}{c}\text{benzothiazole with two } tC_4H_9, C=S-\end{array}\right\}_2 Ni$ |

-continued

| Metallic Salt No. | Chemical Formula |
|---|---|
| III-(16) | $\left\{\begin{array}{c}\text{benzothiazole with } C_8H_{17}, C=S-\end{array}\right\}_2 Co$ |
| III-(17) | $\left\{\begin{array}{c}\text{benzothiazole with } N(C_2H_5)_2, C=S-\end{array}\right\}_2 Zn$ |
| III-(18) | $\left\{\begin{array}{c}\text{benzothiazole with two } N(C_2H_5)_2, C=S-\end{array}\right\}_4 Te.$ |

8. The dry-type toner as claimed in claim 1, further comprising a magnetic material.

9. The dry-type toner as claimed in claim 8, wherein said magnetic material has a particle size ranging from 0.1 $\mu$m to 2 $\mu$m.

10. The dry-type toner as claimed in claim 9, wherein the amount of said magnetic material is in the range of about 20 to about 200 parts by weight to 100 parts by weight of said resin component.

11. The dry-type toner as claimed in claim 1, further comprising carrier particles which are mixed with said dry-type toner to constitute a two-component type developer.

12. The dry-type toner as claimed in claim 1, wherein the amount of said coloring agent is in the range of 1 to 30 parts by weight and the amount of said negative charge controlling agent is in the range of 0.1 to 30 parts by weight, to 100 parts by weight of said resin component.

* * * * *